United States Patent
Sankaran et al.

(10) Patent No.: US 11,944,387 B2
(45) Date of Patent: *Apr. 2, 2024

(54) SYSTEMS AND METHODS FOR RISK ASSESSMENT AND TREATMENT PLANNING OF ARTERIO-VENOUS MALFORMATION

(71) Applicant: HeartFlow, Inc., Redwood City, CA (US)

(72) Inventors: Sethuraman Sankaran, Palo Alto, CA (US); Christopher Zarins, Austin, TX (US); Leo Grady, Darien, CT (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,445

(22) Filed: Mar. 17, 2023

(65) Prior Publication Data

US 2023/0210602 A1    Jul. 6, 2023

Related U.S. Application Data

(63) Continuation of application No. 17/644,762, filed on Dec. 16, 2021, now Pat. No. 11,638,609, which is a
(Continued)

(51) Int. Cl.
*A61B 34/10*     (2016.01)
*A61B 5/00*      (2006.01)
(Continued)

(52) U.S. Cl.
CPC .......... *A61B 34/10* (2016.02); *A61B 5/02007* (2013.01); *A61B 5/4848* (2013.01);
(Continued)

(58) Field of Classification Search
CPC ............................ G06F 19/3437; A61B 34/10
See application file for complete search history.

(56) References Cited

U.S. PATENT DOCUMENTS 8,315,812 B2   11/2012   Taylor
9,042,613 B2    5/2015   Spilker et al.
(Continued)

FOREIGN PATENT DOCUMENTS

EP         2749222 A1    7/2014

OTHER PUBLICATIONS

Kumar, Y. Kiran, Shashi B. Mehta, and Manjunath Ramachandra. "Loop modeling forward and feedback analysis in cerebral arteriovenous malformation." Editorial Preface 4.12 (2013). (Year: 2013).*
(Continued)

*Primary Examiner* — Incent Rudolph
*Assistant Examiner* — Raphael Schwartz
(74) *Attorney, Agent, or Firm* — Bookoff McAndrews, PLLC

(57) ABSTRACT

A computer implemented method for assessing an arterio-venous malformation (AVM) may include, for example, receiving a patient-specific model of a portion of an anatomy of a patient; using a computer processor to analyze the patient-specific model for identifying one or more blood vessels associated with the AVM, in the patient-specific model; and estimating a risk of an undesirable outcome caused by the AVM, by performing computer simulations of blood flow through the one or more blood vessels associated with the AVM in the patient-specific model.

20 Claims, 4 Drawing Sheets

Related U.S. Application Data continuation of application No. 16/999,618, filed on Aug. 21, 2020, now Pat. No. 11,229,486, which is a continuation of application No. 16/376,366, filed on Apr. 5, 2019, now Pat. No. 10,786,308, which is a continuation of application No. 15/977,140, filed on May 11, 2018, now Pat. No. 10,285,762, which is a continuation of application No. 15/807,394, filed on Nov. 8, 2017, now Pat. No. 9,993,303, which is a continuation of application No. 14/842,960, filed on Sep. 2, 2015, now Pat. No. 9,839,483.

(60) Provisional application No. 62/150,701, filed on Apr. 21, 2015.

(51) Int. Cl.
| | | |
|---|---|---|
| A61B 5/02 | (2006.01) | |
| A61B 5/055 | (2006.01) | |
| G06T 7/00 | (2017.01) | |
| G06T 7/20 | (2017.01) | |
| G06T 11/00 | (2006.01) | |
| G16H 30/40 | (2018.01) | |
| G16H 50/30 | (2018.01) | |
| G16H 50/50 | (2018.01) | |

(52) U.S. Cl.
CPC .......... *A61B 5/7275* (2013.01); *G06T 7/0012* (2013.01); *G06T 7/20* (2013.01); *G06T 11/003* (2013.01); *G16H 30/40* (2018.01); *G16H 50/30* (2018.01); *G16H 50/50* (2018.01); *A61B 5/0035* (2013.01); *A61B 5/0073* (2013.01); *A61B 5/055* (2013.01); *A61B 2034/105* (2016.02); *A61B 2505/05* (2013.01); *G06T 2207/10081* (2013.01); *G06T 2207/10088* (2013.01); *G06T 2207/30104* (2013.01)

(56) References Cited

U.S. PATENT DOCUMENTS

| | | |
|---|---|---|
| 2010/0049451 A1 | 2/2010 | Lu et al. |
| 2012/0022843 A1 | 1/2012 | Ionasec et al. |
| 2012/0053918 A1 | 3/2012 | Taylor |
| 2014/0073977 A1 | 3/2014 | Grady et al. |

OTHER PUBLICATIONS

Pollak, Jeffrey S., et al. "Clinical and anatomic outcomes after embolotherapy of pulmonary arteriovenous malformations." Journal of Vascular and Interventional Radiology 17.1 (2006): 35-45. (Year: 2006).*

Guglielmi, Guido. "Analysis of the hemodynamic characteristics of brain arteriovenous malformations using electrical models: baseline settings, surgical extirpation, endovascular embolization, and surgical bypass." Neurosurgery 63.1 (2008): 1-11. (Year: 2008).*

Gao, Erzhen, et al. "Theoretical modelling of arteriovenous malformation rupture risk: a feasibility and validation study." Medical engineering & physics 20.7 (1998): 489-501. (Year: 1998).*

Gao, Erzhen, et al. "Theoretical modelling of arteriovenous malformation rupture risk: a feasibility and validation study." Medical engineering & physics 20.7 (1998): 489-501.

Guglielmi, G. "Electrical Models in the Analysis of Hemodynamic Characteristics of Arteriovenous Malformations: Part 1: Baseline Measurements." Interventional Neuroradiology 12.1 (2006): 9-15.

International Search Report issued in related PCT/US2016/028432, dated Jun. 24, 2016 (13 pgs).

Kroon, Wilco, et al. "Constitutive modeling of cardiac tissue growth." International Conference on Functional Imaging and Modeling of the Heart. Springer, Berlin, Heidelberg, 2007.

Kumar, Y. Kiran, Shashi B. Mehta, and Manjunath Ramachandra. "Loop modeling forward and feedback analysis in cerebral arteriovenous malformation." Editorial Preface 4.12 (2013).

Ogilvy CS, "Radiation therapy for arteriovenous malformations: a review", Neurosurgery, 26(5):725-735, 1990.

Ondrej, Bradac et al.: "Treatment for brain arteriovenous malformation in the 1998-2011 period and review of the literature", ACTA Neurochirurgica., vol. 155, No. 2, Dec. 13, 2012, pp. 199-209.

Orlowski P. et al. "Towards Treatment Planning for the Embolization of Arteriovenous Malformations of the Brain: Intranidal Hemodynamics Modeling", IEEE Transactions on Biomedical Engineering, IEEE Service Center Piscataway, NJ, vol. 58, No. 7; Feb. 24, 2011, pp. 1994-2001.

Smith, F. T., and M.A. Jones. "AVM modelling by multi-branching tube flow: large flow rates and dual solutions." Mathematical Medicine and Biology 20.2 (2003): 183-204.

* cited by examiner

SYSTEMS AND METHODS FOR RISK ASSESSMENT AND TREATMENT PLANNING OF ARTERIO-VENOUS MALFORMATION

RELATED APPLICATIONS

This application is a continuation of and claims the benefit of priority to co-pending U.S. application Ser. No. 17/644,762, filed Dec. 16, 2021, which is a continuation of U.S. application Ser. No. 16/999,618, filed Aug. 21, 2020, now U.S. Pat. No. 11,229,486, which is a continuation of U.S. application Ser. No. 16/376,366, filed Apr. 5, 2019, now U.S. Pat. No. 10,786,308, which is a continuation of U.S. application Ser. No. 15/977,140, filed May 11, 2018, now U.S. Pat. No. 10,285,762, which is a continuation of U.S. application Ser. No. 15/807,394, filed Nov. 8, 2017, now U.S. Pat. No. 9,993,303, which is a continuation of and claims the benefit of priority to U.S. application Ser. No. 14/842,960, filed Sep. 2, 2015, now U.S. Pat. No. 9,839,483, which claims priority under 35 U.S.C. § 119(e) to U.S. Provisional Application No. 62/150,701 filed Apr. 21, 2015, entitled "Systems and Methods for Risk Assessment and Treatment Planning of Arterio-Venous Malformation," the contents of all of which are incorporated herein by reference in their entireties.

FIELD OF THE DISCLOSURE

Various embodiments of the present disclosure relate generally to risk assessment and/or treatment planning of arterio-venous malformations (AVM). More specifically, particular embodiments of the present disclosure relate to systems and methods for using patient-specific physiologic information to identify blood vessels relating to an AVM, and then to evaluate a risk of one or more undesirable patient outcomes caused by the AVM and/or treatment plans associated with the AVM.

BACKGROUND

Arterio-venous malformations are abnormal connections between arteries and veins that may bypass the arterial microcirculation capillaries (capillary arteries). FIG. 1A is a simplified schematic showing a normal arterial and venous network in which an artery 113 receives oxygen-rich blood 109 from a heart 108 and delivers the blood 109 to a healthy capillary bed 112, which in turn delivers oxygen-rich blood 109 to the surrounding tissues. De-oxygenated blood 114 is received by a vein 115 from the bed 112, for return to heart 108.

FIG. 1B, on the other hand, is a simplified schematic of an AVM 119. An artery 113 receives oxygen-rich blood 109 from a heart 108. Blood 109 may pass from the artery 113 to the vein 115 via one or more pre-capillary connections 118, the blood 109 thereby bypassing the normal capillary network 112. In addition, AVM 119 may include a number of enlarged, engorged vessels 117, including new vessels resulting from angiogenesis. AVM 119 also may result in an increase in the size of one or both of artery 113 and vein 115 proximally of AVM 119, and a decrease in the size of artery 113 and vein 115 distally of AVM 119. Further, AVM 119 may include one or more collateral connections 116 between portions of artery 113.

AVMs also may result in less resistance to blood flow, since the pre-capillary arterioles, which provide resistance to blood flow, are bypassed. Patients with AVMs therefore may have a higher blood flow rate and vessels which are larger than normal (such as shown in FIG. 1B, relative to FIG. 1A). The increase in blood flow may result in a higher cardiac output demand, which may result in patients with AVMs having a higher risk of heart failure. The increase in size and number of vascular channels and the increase in total blood flow to an organ, due to an AVM, also can result in an increase in tissue perfusion and an increase in size and growth of tissue. For example, a child with lower limb AVMs may have increased size and growth of the affected limb, with increased bone growth and limb length discrepancy, resulting in the affected limb being longer and the child walking with a limp. Also, thin walled veins resulting from AVMs are exposed to high arterial pressure, thus making them vulnerable to rupture and bleeding.

AVMs may be congenital or acquired, and progressive, stable, or regressive. AVMs may be cosmetically undesirable, and may result in an increased rate of morbidity and/or mortality. Symptoms associated with AVMs may include hemorrhaging, seizures, mass effect (the mass of enlarged blood vessels causing increased intracranial pressure), pain, swelling, hypertrophy, loss of function, ischemia, embolization, and/or heart failure. AVMs may also be symptomatic or asymptomatic throughout a patient's life. An AVM may occur anywhere in the body, but more frequently occurs in the brain and the legs.

Radiographic imaging of AVMs may pose challenges due to the multiplicity of overlapping and layered blood vessels, which may result in difficulty discerning individual blood vessels from each other, and an inability to determine the direction or flow characteristics in the individual blood vessels and blood flow within the AVM. Using some imaging techniques, such as radiographic imaging, angiography, or CT scan, AVMs may appear as a white cloudy mass where the lumens of the individual arteries and/or veins may not be sufficiently delineated.

Thus, a desire exists to obtain improved patient information relating to an AVM, and to provide techniques to assess risk of an AVM and/or plan and assess treatment of an AVM.

SUMMARY

According to an embodiment of this disclosure, one computer implemented method for assessing an arterio-venous malformation (AVM) includes receiving a patient-specific model of a portion of an anatomy of a patient; using a computer processor to analyze the patient-specific model for identifying one or more blood vessels associated with the AVM, in the patient-specific model; and estimating a risk of an undesirable outcome caused by the AVM, by performing computer simulations of blood flow through the one or more blood vessels associated with the AVM in the patient-specific model.

In embodiments, that method may include one or more of the following: the patient-specific model is based on images of at least a portion of a vascular system of the patient; the undesirable outcome includes one or more of rupture of a blood vessel, a mass effect, an increase in venous pressure, and a change in tissue perfusion; performing blood-flow simulations includes calculating stresses within or on blood vessel walls; evaluating one or more treatments of the AVM; identifying one or more blood vessels for treatment, determining an effect on blood flow caused by treatment of the one or more blood vessels, and assessing a change the risk of the undesirable outcome; the treatment includes one or more of embolization of the one or more blood vessels, ablation of the one or more blood vessels, surgical removal of all or part of the AVM, or radiosurgery; and/or predicting progression or regression of the AVM.

In accordance with another embodiment, one system for assessing an arterio-venous malformation (AVM) includes a data storage device storing instructions for assessing an arterio-venous malformation (AVM); and a processor configured to execute the instructions to perform a method including the steps: receiving a patient-specific model of a portion of an anatomy of a patient; using a computer processor to analyze the patient-specific model for identifying one or more blood vessels associated with the AVM, in the patient-specific model; and estimating a risk of an undesirable outcome caused by the AVM, by performing computer simulations of blood flow through the one or more blood vessels associated with the AVM in the patient-specific model.

In embodiments, that system may include one or more of the following: the patient-specific model is based on images of at least a portion of a vascular system of the patient; the undesirable outcome includes one or more of rupture of a blood vessel, a mass effect, an increase in venous pressure, and a change in tissue perfusion; performing blood-flow simulations includes calculating stresses within, on, or external to the blood vessel walls; the processor is further configured for evaluating one or more treatments of the AVM; evaluating the one or more treatments includes identifying one or more blood vessels for treatment, and determining an effect on blood flow caused by treatment of the one or more blood vessels; the treatment includes one or more of embolization of the one or more blood vessels, ablation of the one or more blood vessels, surgical removal of all or part of the AVM, or radiosurgery; and/or the processor is further configured for predicting progression or regression of the AVM.

Another embodiment includes a non-transitory computer-readable medium storing instructions that, when executed by a computer, cause the computer to perform a method for assessing an arterio-venous malformation (AVM). The method may include receiving a patient-specific model of a portion of an anatomy of a patient; using a computer processor to analyze the patient-specific model for identifying one or more blood vessels associated with the AVM, in the patient-specific model; and estimating a risk of an undesirable outcome caused by the AVM, by performing computer simulations of blood flow through the one or more blood vessels associated with the AVM in the patient-specific model.

In embodiments, that method may include one or more of the following: the undesirable outcome includes one or more of rupture of a blood vessel, a mass effect, an increase in venous pressure, and a change in tissue perfusion; evaluating one or more treatments of the AVM, including identifying one or more blood vessels for treatment, determining an effect on blood flow caused by treatment of the one or more blood vessels and assessing a change the risk of the undesirable outcome; and predicting progression or regression of the AVM.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Figure 1A:
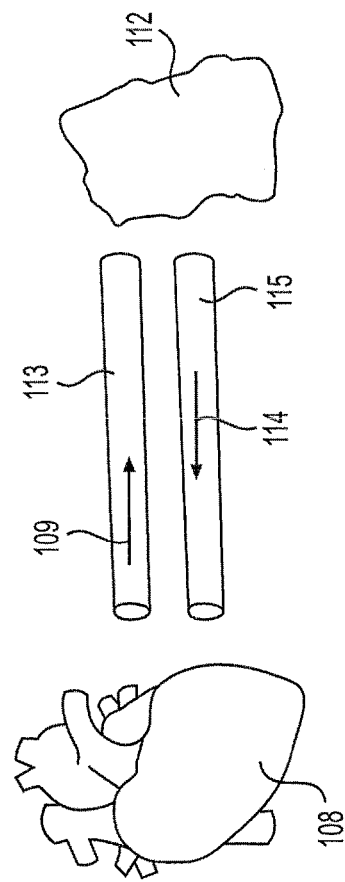
FIGS. 1A and 1B show a normal arterial and venous network, and an AVM, respectively.

Reference will now be made in detail to the exemplary embodiments of the disclosure, examples of which are illustrated in the accompanying drawings. Wherever possible, the same reference numbers will be used throughout the drawings to refer to the same or like parts.

In embodiments of this disclosure, a patient specific vascular and/or anatomical model of an AVM may be constructed from one imaging modality or a combination of imaging modalities. The image acquisition modality may be patient and/or AVM specific. While computer tomography (CT) scans or magnetic resonance imaging (MRI) scans may provide sufficient image resolution for the reconstruction of the arteries and veins in some patients, these scan types may be supplemented with other procedures (e.g., a more invasive procedure), including selectively performing arteriography, venography, and/or injecting a contrast agent to visualize the artery and/or vein and enable accurate modeling of the AVM pathways.

Once the patient-specific model has been constructed, blood flow characteristics (e.g., blood flow rate, blood pressure, and any related quantities, including wall shear stresses) may be calculated by, for example, assigning appropriate boundary conditions and solving the Navier-Stokes equations. A model of a blood vessel wall with appropriate material properties also may be used with fluid-structure interaction simulations to determine an accurate prediction of intramural stress. In addition, modeling growth and remodeling mechanisms in the AVMs may be used to estimate the changes in the blood vessel radius and blood vessel thickness due to intramural and wall shear stresses acting on the blood vessel walls. Alternatively, reduced order models or machine learning methods may be used to compute blood flow characteristics. Quantities including the particle residence time and the oscillatory shear index may also be calculated from the solution of the Navier-Stokes equations.

Estimates of patient risk due to the AVM may be based on (a) purely anatomical information, and/or metabolic and physiologic information, and/or (b) functional analysis through blood flow simulations. A risk estimate based on anatomical information may depend on the location of the AVM, its proximity to critical organs and/or blood vessels (greater risk when the AVM is proximate to an organ or vessel), the difficulty in accessing the AVM locations within the body (difficult to reach AVMs may cause an increased risk of an undesirable event during the treatment procedure), the size (diameter) of the feeding arteries, branches, collaterals, connecting vessels and draining veins; the location of vessels; the thickness and/or the composition of the vessel wall; the size, location and/or number of communicating channels between the artery and the vein; the organ or other anatomical structure being supplied by the involved vessels; and the anatomy of surrounding structures or organs. The risk of blood vessel rupture may be determined based on blood flow simulations and vessel wall characteristics, including thickness, structure, and/or composition of the vessel wall. Thin walled veins and degenerated or injured vessels are more prone to rupture. For example, vessel rupture risk may be increased by forces acting within or on the blood vessel walls, including intramural and transmural stresses acting on the vessel wall, and/or decreases in strength or structural integrity of the wall. Wall shear stresses can stimulate vessel enlargement, which can be accompanied by thinning of the wall, also leading to rupture. Forces acting on blood vessel walls may be calculated using the blood pressure and the tangential gradient of blood velocity along the vascular walls, and solid mechanics of vessel wall characteristics.

The benefits of one or more treatments, including interventional procedures such as embolization of the blood vessels feeding the AVM, may be estimated/determined by evaluating one or more of the reduction in AVM blood flow, transmural, intramural, and wall shear stresses, and the restoration of venous pressure and tissue perfusion to nominal values. This may be performed by first modeling the patient-specific anatomical geometry post-treatment, performing hemodynamic simulations (or using reduced order models and/or machine learning methods), and subsequently, evaluating the factors that were quantified at a pre-treatment stage as compared to the post-treatment stage. The risk factor of no intervention may also be quantified by evaluating the above criteria without any modification in the patient-specific anatomical geometry.

Any of the methods and systems disclosed in U.S. Pat. Nos. 8,315,812 and 9,042,613 and U.S. Patent Application Publication No. 2014/0073977, for preparing the patient-specific models from, for example patient-specific physiologic images/data, determining blood flow characteristics, performing blood flow simulations, and/or evaluating pre- and post-treatment planning may be used with the methods and systems of the present disclosure. The complete disclosures of these patents and published application are incorporated by reference herein in their entirety.

Figure 2:
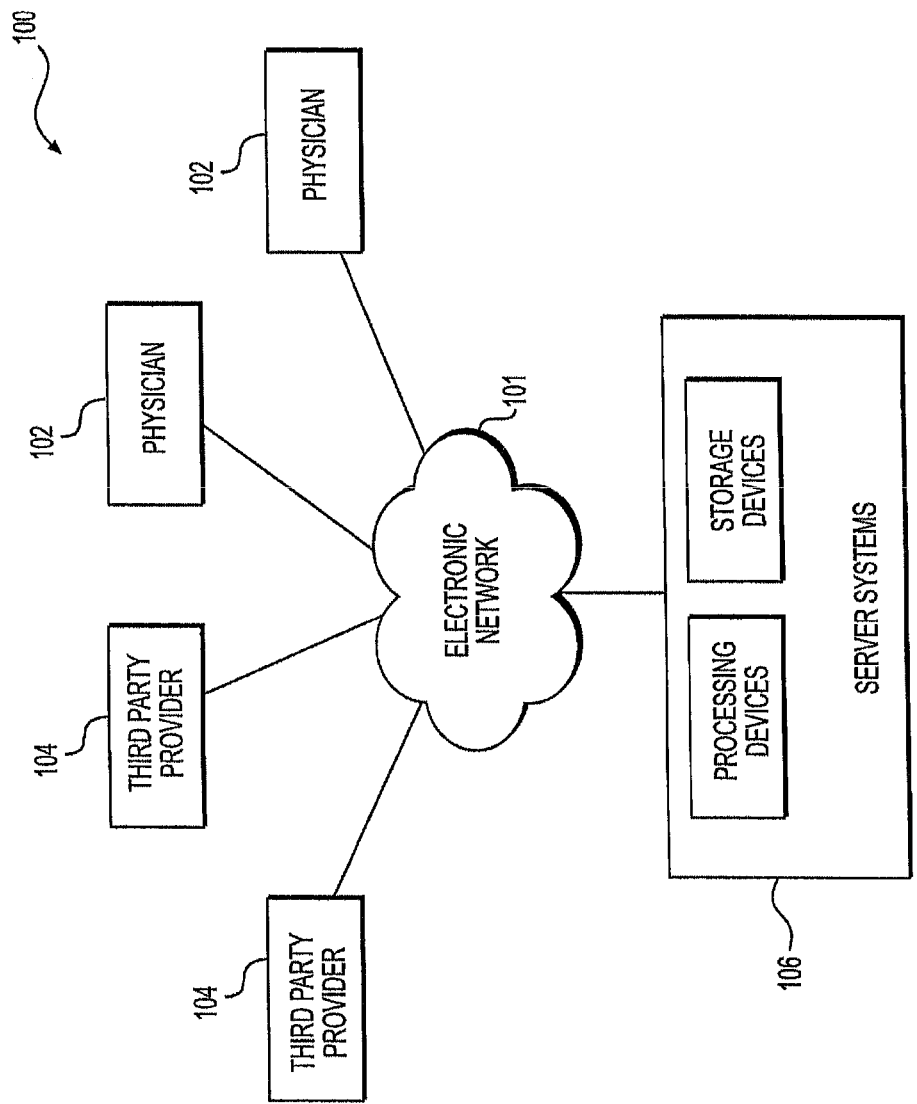
FIG. 2 is a block diagram of an exemplary system and network for assessment and/or guiding diagnosis and/or treatment of an AVM, according to an exemplary embodiment of the present disclosure.

FIG. 2 depicts a block diagram of an exemplary system 100 for diagnosing, assessing, and/or treatment planning of an AVM, according to an exemplary embodiment. Specifically, FIG. 2 depicts a plurality of physicians 102 and third-party providers 104, any of whom may be connected to an electronic network 101, such as the Internet, through one or more computers, servers, and/or handheld mobile devices. Physicians 102 and/or third-party providers 104 may create or otherwise obtain images of one or more patients' anatomies. The physicians 102 and/or third-party providers 104 also may obtain any combination of patient-specific information, such as age, medical history, blood pressure, blood viscosity, patient activity or exercise level, etc. Physicians 102 and/or third-party providers 104 may transmit the anatomical images and/or patient-specific information to server systems 106 over the electronic network 101. Server systems 106 may include storage devices for storing images and data received from physicians 102 and/or third-party providers 104. Server systems 106 may also include processing devices for processing images and data stored in the storage devices.

Figure 3:
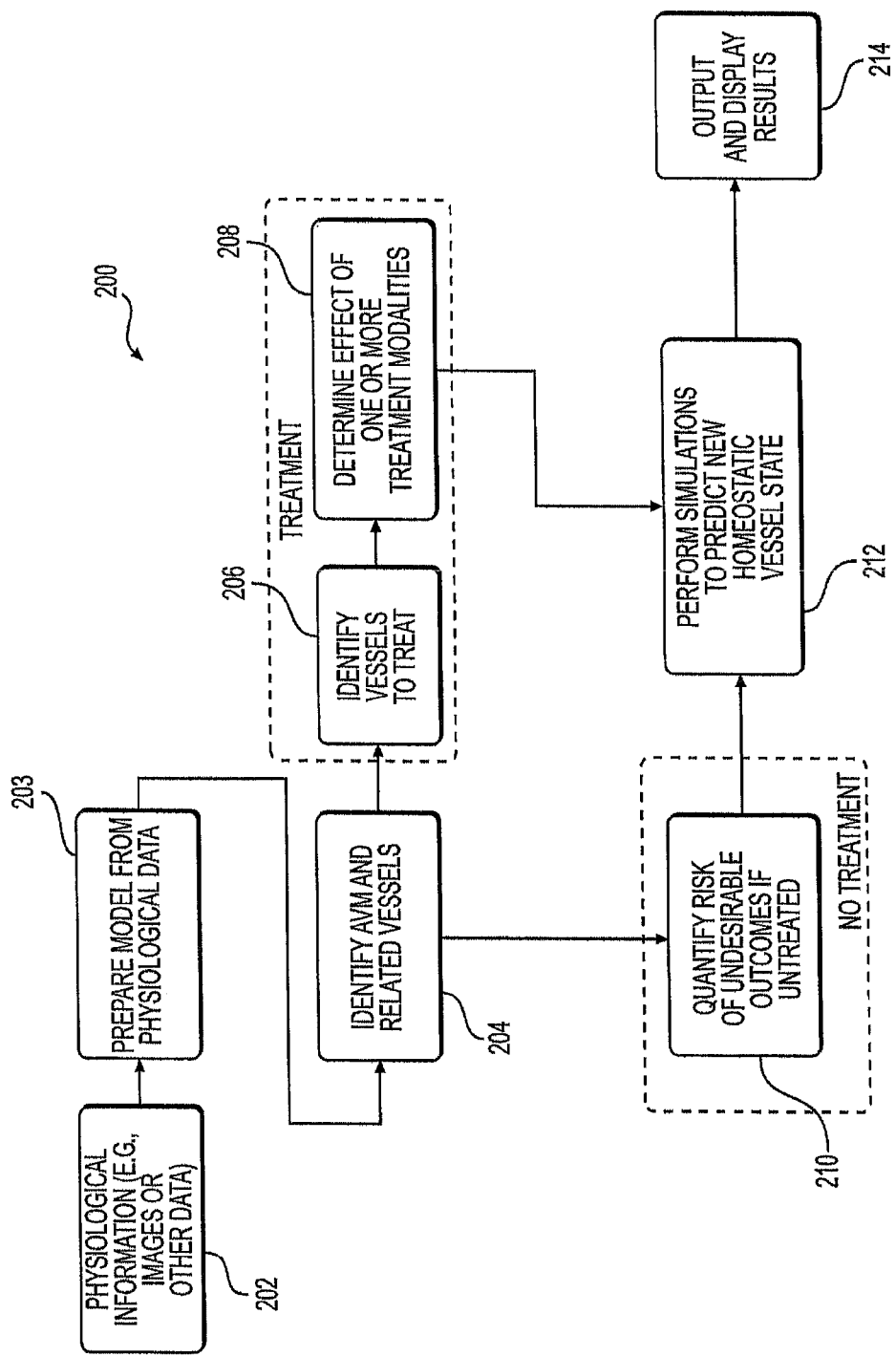
FIG. 3 is a flow chart of an exemplary method of assessment and/or treatment planning of an AVM, according to an exemplary embodiment of the present disclosure.

FIG. 3 depicts an embodiment of an exemplary method 200 for assessment and/or treatment planning of an AVM. The method of FIG. 3 may be performed by server systems 106, based on information, images, and data received from physicians 102 and/or third-party providers 104 over electronic network 101.

In an embodiment, step 202 may include receiving physiologic information of a patient. The physiologic information may include imaging data of a patient's brain, leg, or other portion of the body. The data may derive from one or more imaging modalities (e.g., computed tomography (CT) scans, magnetic resonance imaging (MRI), ultrasound) and other visualization techniques, including arteriography, venography, and/or injecting a contrast agent to visualize the artery and/or vein. Other physiologic information that may be received includes blood flow rates and/or blood pressure measurements at one or more locations within the target vasculature. The received physiologic information may be stored in an electronic storage medium including, but not limited to, a hard drive, network drive, cloud drive, mobile phone, tablet, or the like.

In one embodiment, step 203 may include generating a patient-specific geometric model and/or vascular model from the patient-specific physiologic information based on any known technique, including the techniques described in U.S. Pat. No. 8,315,812 incorporated above. The patient-specific model may be generated at the server system 106 or elsewhere and received over an electronic network (e.g., electronic network 101).

Figure 1B:
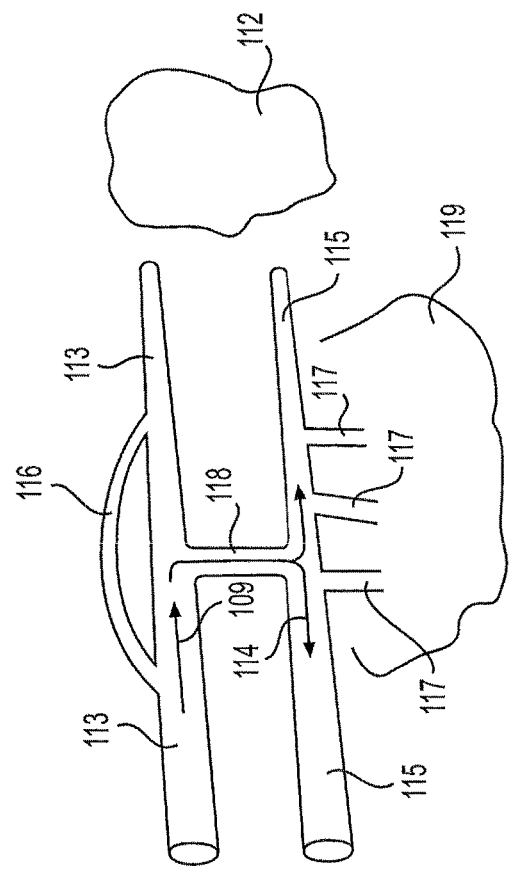

In one embodiment, step 204 may include identifying the location of the one or more AVMs, and performing segmentation of the blood flow lumens leading to and from the AVM. For example, step 204 may include identifying and optionally highlighting and displaying the AVM, some or all of the vessels feeding blood to the AVM from one or more arteries, some or all of the vessels draining blood from the AVM to one or more veins, and any corresponding parent blood vessels. The display may resemble FIG. 1B, for example.

After identifying the AVM and related vessels in step 204, a method according to an embodiment of this disclosure branches into one or both of two steps, one step evaluating treatment options and another step assessing the risk of not treating the AVM. One or both of these steps may be performed in embodiments of this disclosure.

The treatment steps are shown in steps 206 and 208 of FIG. 3. Step 206 may include identifying and optionally displaying one or more of the blood vessels identified in step 204 that will undergo a treatment. For example, the identified blood vessels may include one or more feeding vessels, draining vessels, or corresponding parent vessels.

In one embodiment, step 208 may include determining the flow effect of the one or more treatment modalities in the one or more identified vessels. The treatment may include embolization or ablation of one or more vessels, surgical removal of all or part of the AVM, radiosurgery, or any other method that affects the blood flow within the vessels/AVM, including, for example, elimination of the direct communication between artery and vein by a direct repair. A direct repair can be performed, for example in a traumatic AV fistula where the hole in the artery and vein are repaired, or when an AV dialysis shunt is removed and the vessels are repaired. For example, in some embodiments, step 208 may include quantifying the benefit and/or risk of embolization of the feeding vessels. Step 208 may further include providing and assessing a variety of treatment options relative to one another and/or relative to not treating the AVM and surrounding vessels. For example, the treatment strategy may involve either the embolization of a subset of the feeding blood vessels, a subset of the draining blood vessels, a combination thereof, or excising all or a portion of the AVM. Such combinations may be explored exhaustively or by first identifying the larger blood vessels of the AVM and sequentially progressing to the smaller blood vessels until a desired hemodynamic state is achieved. Treatment benefits may be computed by simulating patient-specific vascular geometry post treatment. Blood flow simulations may be performed in the modified geometry by, for example, solving 3D Navier-Stokes equations, using reduced order models, or using machine learning methods. Any of the methods and systems disclosed in U.S. Pat. Nos. 8,315,812 and 9,042,613 and U.S. Patent Application Publication No. 2014/0073977 incorporated above, for performing blood flow simulations may be used with the methods and systems of the present disclosure. In addition, as described below, a number of quantities may be calculated based on not treating the AVM or surrounding vessels. Those quantities, such as rupture risk, venous pressure, and capillary perfusion levels, for each treatment strategy may be calculated in step 208.

As mentioned above, embodiments of this disclosure may assess the risk of undesirable outcomes if no treatment is performed on the AVM. Undesirable outcomes include blood vessel rupture, mass effects, high venous pressure, and alteration in tissue perfusion. The step of assessing the risk of these outcomes, shown as step 210 in FIG. 3, may be performed with or without treatment steps 206, 208. As with the treatment steps, steps 202, 203, and 204 are performed first.

In some embodiments, step 210 includes quantifying the risk of an undesirable outcome (rupture, mass effect, etc.) with no treatment of the AVM, by performing blood-flow simulations, including for example, calculating intramural and wall shear stresses and/or vessel wall properties (e.g. strength of the vessel wall) from blood flow simulations. Patient risk may be quantified by either using anatomical information, functional information, or a combination thereof. The risk of a rupture of a vessel may be based on the probability that the AVM may rupture around a vital organ or artery, or compress or otherwise impact the surrounding tissue. The rupture risk may be representative of internal and external forces acting on the walls of the one or more blood vessels which comprise the AVM.

The risk of rupture may be quantified by first performing patient-specific simulations of blood flow using boundary conditions derived from either (a) flow rates and/or internal pressures measured in step 203 or (b) resistance boundary conditions scaled based on the size of the AVM and the feeding and draining vessels, vessel wall characteristics, and extravascular forces acting on the vessels and/or AVM. Alternatively, reduced order models or machine learning methods may be used to perform blood flow simulations. The blood flow rates and/or blood pressures from the hemodynamic simulations may be used to calculate the wall shear stress and intramural stress within one or more of the plurality of blood vessels. The wall shear stress may be calculated by calculating the magnitude of the derivative of blood velocity along the blood vessel walls, while intramural stress may be calculated using the blood pressure and the radius and thickness of the blood vessel (vessel thickness may be modeled as 10% of radius if a measurement is unavailable). Alternatively, intramural stresses may be calculated by performing fluid-structure interaction simulations by assuming a Young's modulus for the blood vessel wall. The risk of blood vessel rupture may be quantified by the probability that the net wall stress may exceed the wall strength.

An undesirable mass effect that may result by not treating an AVM may include the compression, displacement, encroachment, or irritant (i.e., trigger source for seizures) of blood vessels. The mass effect may be included in an analysis by modeling the stiffness of surrounding tissues and/or structures to model the interaction of various forces on the AVM in relation to surrounding tissues. Mass effects may be quantified by the displacement of the AVM and the net forces exerted on the surrounding tissues.

In embodiments of the disclosure, after assessing treatment options in steps 206, 208 and/or undesirable outcomes of no treatment in step 210, step 212 may include performing growth and remodeling simulations to predict the new homeostatic vessel state. Step 212 may include predicting progression and/or regression of the AVM. The progression and/or regression of the AVM may be modeled by solving stress equilibrium equations of the blood vessel walls, and computing the AVM configuration (radius and thickness of the blood vessels) at a homeostatic state. This may be calculated, for example, by first evaluating the wall shear stresses and the intramural stresses from the blood flow simulations. Subsequently, the remodeling of the lumen geometry may be performed using either reduced order models, finite element simulations, machine learning methods, or a combination thereof. Reduced order one dimensional equations for predicting the remodeling of radius and thickness of blood vessels may be written as $P=\sigma r/t$ and $\tau=2\mu Q/\pi r^3$, where P is blood pressure, $\sigma$ is the intramural stress, r is the lumen radius, t is the wall thickness, Q is the lumen flow rate, $\tau$ is the wall shear stress, and $\mu$ is the dynamic viscosity of blood. Additionally, progression/regression modeling may the addition of data from serial imaging studies of the same patient/AVM at one or more subsequent times, and using that information to inform/update the model.

Alternatively, one embodiment of step 212 may include using a numerical method including finite element, finite differences, and/or spectral expansion methods to predict remodeling. This may involve first creating a geometric model of the lumen blood vessel wall, then meshing the resultant model and solving the partial differential equations governing stress equilibrium and mass conservation to achieve a homeostatic state. Another alternative may be to use machine learning methods where the relationship between the thickness and radius of the blood vessels due to changes in flow on a number of different AVMs may be first learned from data. This may be performed by constructing a map between geometric variables, blood flow, blood pressure, and the remodeled blood vessel radius and wall thickness. Subsequently, this map may be used to predict the remodeled geometry based on all the input features, including features extracted from geometry (e.g., original lumen radius, size and number of draining blood vessels, size and number of feeding blood vessels, resistance of downstream vasculature, blood supply, and parameters derived from hemodynamics including blood pressure, and wall shear stress). An increase in the overall AVM radius and/or the radius of its individual vessels may indicate progression and a reduction may indicate regression.

In one embodiment, step 214 may include outputting a plurality of factors to a display, including but not limited to, progression and/or regression of vessel size and states, intramural stresses and wall shear stresses of the vessels, vessel location and proximity to vital organs, pressure of the blood in the veins, and capillary perfusion. One representation may be an electronic chart summarizing the benefits and/or risks of one or more surgical interventions or other treatments, and the risk of leaving the AVM untreated. The following variables may be examples of variables that may be included in a displayed output: (a) differences in rupture risk before and after treatment, (b) location of critical organs and/or blood vessels in the vicinity of the AVM, (c) difficulty in site access which may be quantified using tortuosity of the vessel and the size of the AVM, (d) a patient-specific map of wall shear stress and intramural stress before and after intervention, and (e) mass effect characteristics quantifying wall displacement (e.g., encroachment into surrounding tissue) and forces exerted on the tissue.

The predicted remodeled geometry based on the analysis in step 212 may be output to a display in step 214. The output may be the new remodeled patient-specific geometry or the changes in vessel geometry at salient locations including the vessels feeding or draining the AVM. In addition, the venous pressure and tissue blood perfusion may be output to a display. Any other output that may be available from the simulation may be included.

Figure 4:
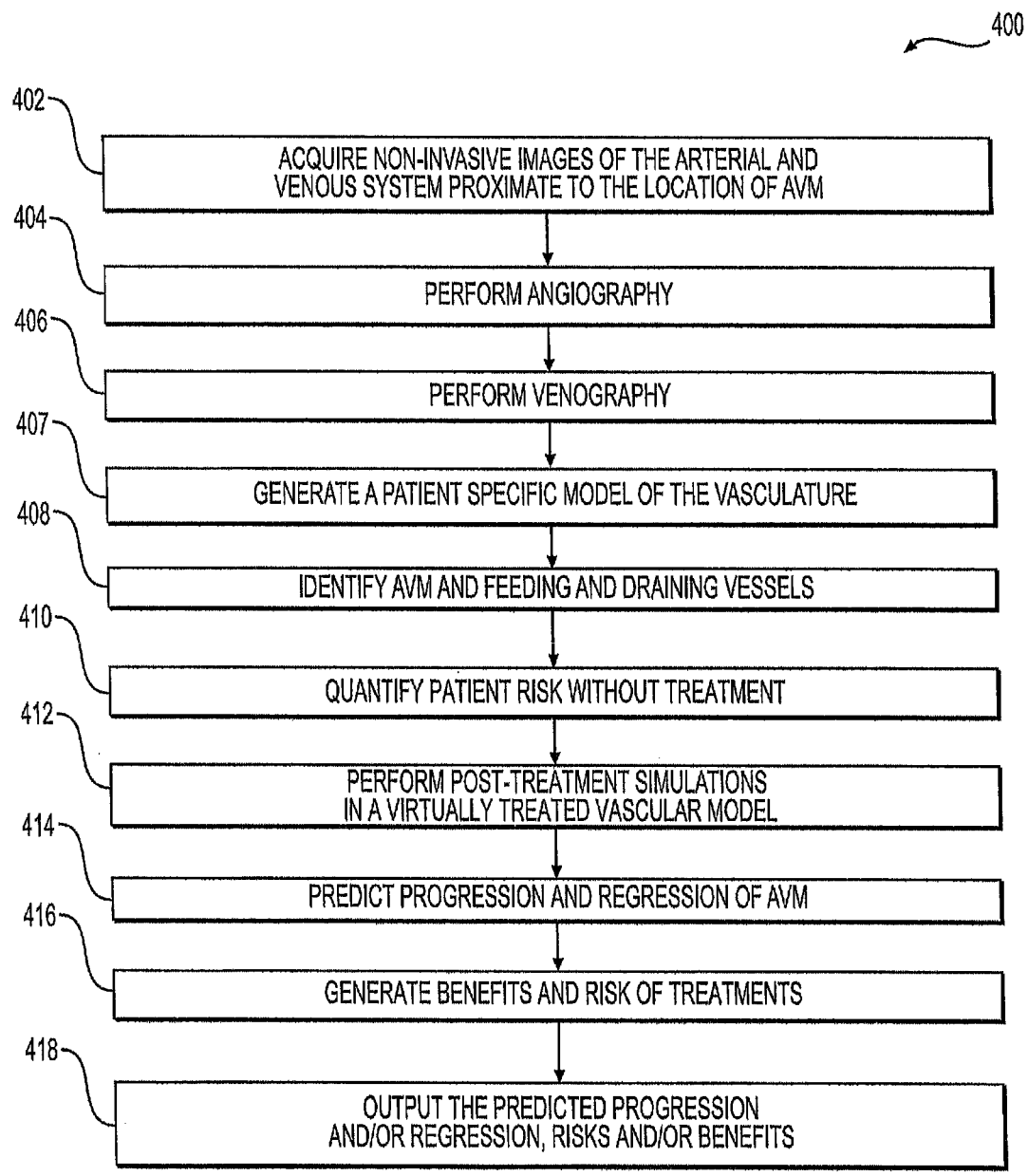
FIG. 4 is a flow chart of an exemplary method of assessment and/or treatment planning of an AVM, according to an exemplary embodiment of the present disclosure.

FIG. 4 depicts an exemplary, more specific embodiment of a method 400 for providing risk assessment and treatment option assessment of cerebral AVMs either using MRI or selective angiography techniques. Cerebral AVMs may involve abnormal connections between the arteries and veins of the brain. Those connections shunt the capillary vessels and may pose risks such as cerebral hemorrhaging and epilepsy. The method depicted in FIG. 4 may include any of the steps and features described above in connection with FIG. 3 and within a system described in FIG. 2.

Step 402 of method 400 may include acquiring non-invasive images of the arterial and venous system proximate the location of an AVM. In an embodiment, this may include obtaining one or more digital representations/images encompassing some or all of the arterial and venous vasculature system of the brain, including such vasculature encompassing the location of the AVM. More specifically, step 402 may include collecting input data acquired using a non-invasive technique including MRI or CT scans, ultrasound (extra and intravascular), 3D ultrasound, duplex ultrasound and/or optical coherence tomography (OCT). The locations of AVMs may be characterized by the number and size of the blood vessels that connect arteries to veins.

Optionally, step 404 may include performing a selective angiography. A non-invasive method, such as MRI or CT scan, may show only a white spot or blurred area near the location of an AVM, due to multiple overlapping vessels of various sizes comprising the AVM obscuring visualization of individual vessels within the AVM or due to limitations of the resolution of the imaging modality. In such cases, step 404 may include performing a selective angiography where one or more blood vessels may be clipped and a contrast agent may be selectively administered to a parent artery to aid in identification of the vessels. This may enable isolation of the blood vessels and aid in an accurate patient-specific reconstruction of the blood vessels near the AVM site.

Optionally, step 406 may include performing a selective venography to isolate blood vessels and improve visualization. This step may be performed with or without the angiography of step 404. The draining of veins of the AVM, which may have high blood flow, may be better visualized and reconstructed using contrast enhanced 3D MR venography. Other visualization techniques may be used to isolate vessels and improve visualization of vessels proximate an AVM. In addition, this step may include a variety of techniques for directly inputting vessels or segments of vessels which cannot be visualized.

Step 407 includes generating a patient specific model of the vasculature proximate the AVM, based on the images and other data obtained in steps 402, 404, and 406, using any suitable technique, such as ones mentioned above and in incorporated by reference U.S. Pat. Nos. 8,315,812 and 9,042,613 and U.S. Patent Application Publication No. 2014/0073977.

Step 408 may include identifying the blood vessels within the model that may be responsible for feeding and draining blood to and from the AVM. These vessels may be identified by examining all of the blood vessels connecting the AVM identified in steps 402, 404, and 406 to blood vessels which may not be a part of the AVM. Step 408 may further include visualizing the feeding and draining blood vessels in a display. The AVM itself may be localized with an image segmentation algorithm, an image threshold algorithm, or any other suitable method.

Step 410 may include quantifying patient risk without treatment of the cerebral AVM, by performing blood flow simulations. Patient risk may be quantified using either anatomical information or functional information, as discussed above. For example, the Spetzler-Martin grade may be used in estimating the risk to a patient caused by an AVM. The Spetzler-Martin grading system allocates points for various features of intracranial AVMs, resulting in a score between 1 and 5. The score correlates with operative/treatment outcome. The factors that may be considered in quantifying patient risk in the Spetzler-Martin grading system include, but are not limited to: (i) the size of the AVM (1, 2, or 3 points depending on the size), (ii) the presence of an adjacency eloquent cortex (e.g., the cortex may be involved in sensory processing—1 point), and (iii) the presence of draining veins (superficial—0 points, and/or deep vein—1 point). The Spetzler-Martin grade may be first calculated and stored in a memory.

Step 410 may further include performing blood flow simulations which may aid in predicting functional estimates of patient risk. The blood flow simulations may be performed through the cerebral AVM using the patient-specific model reconstructed in step 407, and subsequently creating a finite element model and solving the Navier-Stokes equations for mass and momentum balance of blood. Inlet flow boundary conditions may be assigned if available, and a pressure boundary condition may be assigned at the arterial inlets to the model. Pressure or resistance boundary conditions may be applied at the venous outlets that model the resistance downstream of the veins to their draining site.

Alternatively, step 410 may include solving one dimensional blood flow equations, and/or reduced order models including solving the Hagen-Pouiseuille equations with stenosis models. Bernoulli's equations also may be used. Alternatively, a machine learning approach may be used. The net stress acting on the vascular wall (including both intramural and wall shear stress) may be calculated from the blood velocities and from material properties of the vascular wall. Furthermore, the mass effect may be calculated by assigning material properties to the tissue surrounding the cerebral system, and computing the forces exerted by the motion of cerebral AVMs on the external tissue using Fluid-Structure interaction simulations.

In one embodiment, step 412 may include performing post-treatment simulations. To quantify the risk of intervention, blood flow simulations may be performed in a virtually treated vascular model. Treatment options may be based on embolization of multiple combinations of draining and feeding vessels to the AVM to ensure minimization of risk factors. Simulations may be performed in the post-treatment vascular model, and the quantities identified above in step 410 may be computed. Alternatively, step 412 may include using machine learning methods or reduced order models. The risk of rupture may be calculated in the post-treatment geometry.

Step 412 may be repeated for any number of candidate treatment configurations as identified by the physician. An optimization method (e.g., pattern search methods or Nelder-Mead algorithm) may be used to automatically calculate the best configuration that minimizes the risk of rupture or any other undesirable outcome.

In one embodiment, step 414 may include predicting progression and regression of the AVM. Step 414 may further include constructing a finite element mesh of the vessel walls and performing a fluid structure interaction simulation to compute wall shear stress and intramural stress. Subsequently, progression and regression of the AVM may be predicted by solving the growth and remodeling equations on the vessel wall and calculating the radius and thickness of the AVM or vessels comprising the AVM at homeostasis. Step 414 also may involve modeling the cerebral vascular wall properties, imposing the homeostatic stress state in the vascular walls, and solving the stress equilibrium equations until the stresses reach the homeostatic state. The resultant geometry (blood vessel radius and thickness) may represent the remodeled homeostatic state. An increase in the radius of the vessels may imply a progression of the AVM, and a reduction thereof may indicate a regression in the AVM.

Step 416 may include generating a list of benefits and/or risks of one or more treatment methods and/or of not treating the AVM. A list of factors that may influence the treatment plan may be output to the physician. The list may include, but is not limited to: (a) anatomical risk factors including the Spetzler-Martin grade, which as described above may be based on AVM size or size of the vessels comprising the AVM (e.g., small, medium or large), location in the brain, and whether superficial or deep veins are involved; (b) functional risk factor using hemodynamic simulations and quantifying difference in rupture risk with and without treatment; (c) difference in venous pressure post- and pre-treatment; (d) difference in tissue perfusion before and after treatment; and (e) predicting the remodeled blood vessel radius and thickness, and highlighting the differences in/around the AVM. Step 418 may include outputting the predicted progression and/or regression and/or risks and benefits to an electronic storage medium or to a display. This method also may include follow-up imaging to evaluate the results of treatment and predict risk of recurrences.

It will be apparent to those skilled in the art that various modifications and variations can be made in the disclosed retrieval devices and methods without departing from the scope of the disclosure. Other aspects of the disclosure will be apparent to those skilled in the art from consideration of the specification and practice of the features disclosed herein. It is intended that the specification and examples be considered as exemplary only.

What is claimed is:

1. A computer implemented method for assessing an arterio-venous malformation (AVM), the method comprising:
   receiving image data of at least a portion of a vascular system of a patient, including one or more blood vessels associated with the AVM;
   generating a patient-specific three-dimensional anatomic model of the portion of the vascular system of the patient, using the received image data;
   identifying, using a computer processor, one or more larger blood vessels among the one or more blood vessels associated with the AVM; and
   generating a treatment recommendation for treating the AVM, based on the identified one or more larger blood vessels, wherein generating the treatment recommendation includes predicting an increase or decrease in (a) a radius of the AVM or (b) a radius of the one or more blood vessels associated with the AVM.

2. The method of claim 1, further comprising:
   using a stress equilibrium equation, calculating a vessel wall property of one or more vessel walls of the one or more blood vessels; and
   evaluating one or more treatments of the AVM based on the calculated vessel wall properties and based on the identified one or more larger blood vessels.

3. The method of claim 2, wherein evaluating the one or more treatments includes:
   determining an effect on blood flow caused by the one or more treatments; and
   assessing a change in a risk of an undesirable outcome based on the determined effect.

4. The method of claim 2, wherein the vessel wall property includes a vessel wall thickness, vessel wall structure, or vessel wall composition.

5. The method of claim 1, wherein generating the treatment recommendation for treating the AVM includes assessing a proximity of the identified one or more larger blood vessels relative to an organ or another blood vessel.

6. The method of claim 1, wherein generating the treatment recommendation includes weighing a list of factors comprising one or more of:
   anatomical risk factors, including Spetzler-Martin grade;
   functional risk factors;
   a difference in a venous pressure post- and pre-treatment;
   a difference in tissue perfusion before and after treatment; or
   a prediction of a remodeled blood vessel radius and thickness.

7. The method of claim 1, further comprising modeling a stiffness of tissues surrounding the AVM.

8. The method of claim 1, further comprising calculating a displacement of the AVM and one or more forces exerted on tissues surrounding the AVM.

9. The method of claim 1, further comprising performing growth or remodeling simulations to predict a hemostatic vessel state of the one or more blood vessels.

10. The method of claim 1, further comprising quantifying a risk of undesirable outcomes for a situation in which the AVM is not treated.

11. A system for assessing an arterio-venous malformation (AVM), the system comprising:
    at least one data storage device storing instructions for assessing the AVM; and
    at least one processor configured to execute the instructions to perform a method comprising:

receiving image data of at least a portion of a vascular system of a patient, including one or more blood vessels associated with the AVM;

generating a patient-specific three-dimensional anatomic model of the portion of the vascular system of the patient, using the received image data;

identifying, using a computer processor, one or more larger blood vessels among the one or more blood vessels associated with the AVM; and generating a treatment recommendation for treating the AVM, based on the identified one or more larger blood vessels, wherein generating the treatment recommendation includes predicting an increase or decrease in (a) a radius of the AVM or (b) a radius of the one or more blood vessels associated with the AVM.

12. The system of claim 11, wherein the method further comprises:

using a stress equilibrium equation, calculating a vessel wall property of one or more vessel walls of the one or more blood vessels; and evaluating one or more treatments of the AVM based on the calculated vessel wall properties and based on the identified one or more larger blood vessels.

13. The system of claim 12, wherein evaluating the one or more treatments includes:

determining an effect on blood flow caused by the one or more treatments; and assessing a change in a risk of an undesirable outcome based on the determined effect.

14. The system of claim 11, wherein generating the treatment recommendation includes weighing a list of factors comprising one or more of:

anatomical risk factors, including Spetzler-Martin grade; functional risk factors;

a difference in a venous pressure post- and pre-treatment;

a difference in tissue perfusion before and after treatment; or a prediction of a remodeled blood vessel radius and thickness.

15. The system of claim 11, wherein the method further comprises modeling a stiffness of tissues surrounding the AVM.

16. The system of claim 11, wherein the method further comprises: calculating a displacement of the AVM and one or more forces exerted on tissues surrounding the AVM.

17. A non-transitory computer readable medium storing computer-executable programming instructions for performing a method of non-invasively assessing a patient, the method comprising:

receiving image data of at least a portion of a vascular system of the patient, including one or more blood vessels associated with an arterio-venous malformation (AVM);

generating a patient-specific three-dimensional anatomic model of the portion of the vascular system of the patient, using the received image data;

identifying, using a computer processor, one or more larger blood vessels among the one or more blood vessels associated with the AVM; and generating a treatment recommendation for treating the AVM, based on the identified one or more larger blood vessels, wherein generating the treatment recommendation includes predicting an increase or decrease in (a) a radius of the AVM or (b) a radius of the one or more blood vessels associated with the AVM.

18. The non-transitory computer readable medium of claim 17, wherein the method further comprises:

using a stress equilibrium equation, calculating a vessel wall property of one or more vessel walls of the one or more blood vessels; and evaluating one or more treatments of the AVM based on the calculated vessel wall properties and based on the identified one or more larger blood vessels.

19. The non-transitory computer readable medium of claim 18, wherein evaluating the one or more treatments includes:

determining an effect on blood flow caused by the one or more treatments; and assessing a change in a risk of an undesirable outcome based on the determined effect.

20. The non-transitory computer readable medium of claim 17, wherein generating the treatment recommendation includes weighing a list of factors comprising one or more of:

anatomical risk factors, including Spetzler-Martin grade; functional risk factors;

a difference in a venous pressure post- and pre-treatment;

a difference in tissue perfusion before and after treatment; or a prediction of a remodeled blood vessel radius and thickness.

* * * * *